United States Patent [19]

Ruff

[11] Patent Number: 4,832,040

[45] Date of Patent: May 23, 1989

[54] NON-BUNCHING CINCH RING FOR SELF-APPLIED BLOOD PRESSURE CUFF

[75] Inventor: Gray E. Ruff, Hillsboro, Oreg.

[73] Assignee: SpaceLabs, Inc., Bothell, Wash.

[21] Appl. No.: 76,455

[22] Filed: Jul. 22, 1987

[51] Int. Cl.⁴ .............................................. A61B 5/02
[52] U.S. Cl. ................................... 128/686; 128/327
[58] Field of Search ...................... 128/672, 677–686, 128/327; 24/197–200, 265 BC

[56] References Cited

U.S. PATENT DOCUMENTS

| | | | |
|---|---|---|---|
| 2,156,870 | 5/1939 | Rineer et al. | 128/327 |
| 2,480,430 | 8/1949 | Walters | 128/327 |
| 2,713,708 | 7/1955 | Anderson | 24/198 |
| 3,005,454 | 10/1961 | Bird | 24/198 |
| 3,450,136 | 6/1969 | Anderson | 128/327 |
| 3,587,595 | 6/1971 | Ceravolo | 128/327 |
| 3,633,567 | 1/1972 | Sarnoff | 128/327 |
| 4,300,573 | 11/1981 | Rebbe et al. | 128/686 |
| 4,429,699 | 2/1984 | Hatschek | 128/681 |

FOREIGN PATENT DOCUMENTS 8300426  2/1983  U.S.S.R. ............................ 128/686

Primary Examiner—Max Hindenburg
Assistant Examiner—Angela D. Sykes
Attorney, Agent, or Firm—Seed and Berry

[57] ABSTRACT

A self-adjusting blood pressure cuff assembly. A cinch ring at the fixed end of the blood pressure cuff assembly has at least one lateral extension disposed away from the direction of the fixed end of the flexible belt of the cuff assembly. The longitudinal extension has two longitudinally directed sides. Placing reinforcing stitches closely adjacent the longitudinally directed sides substantially restricts transverse movements of the cinch ring with respect to the flexible band. In a preferred embodiment, a tag piece, passing through the slot of the cinch ring and covering the lateral extension, is reinforced stitched to the outward cover of the elongated flexible band of the blood pressure cuff assembly. In this way, an end of an inflatable bladder can be caused to be adjacent to the loop of material forming the fixed end of the flexible band. The bladder can be placed between the skin of the person wearing the blood pressure cuff assembly and the lateral extension of the cinch ring in order to eliminate any discomfort caused by pressing the longitudinal extension against the person.

21 Claims, 3 Drawing Sheets

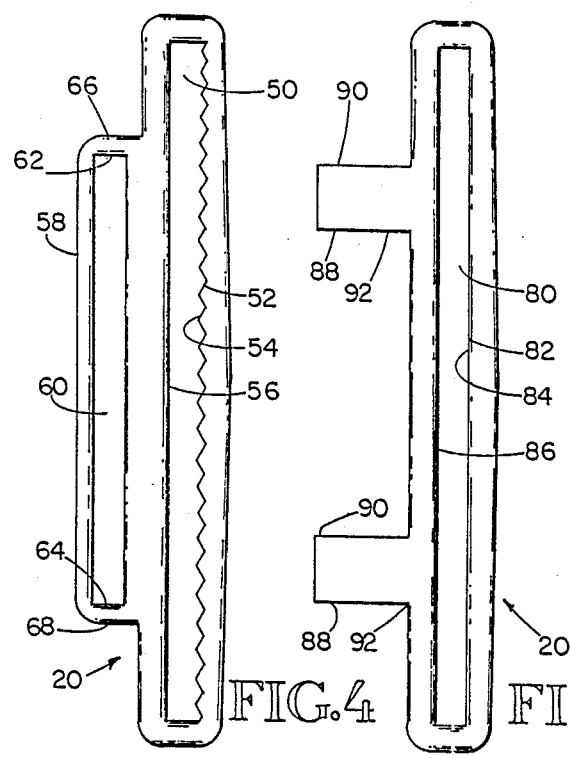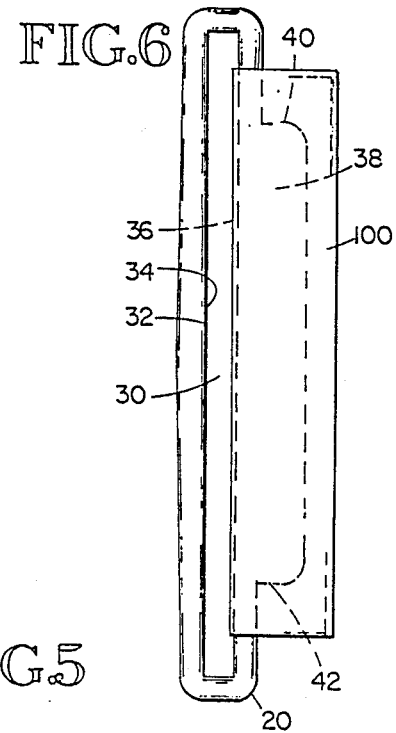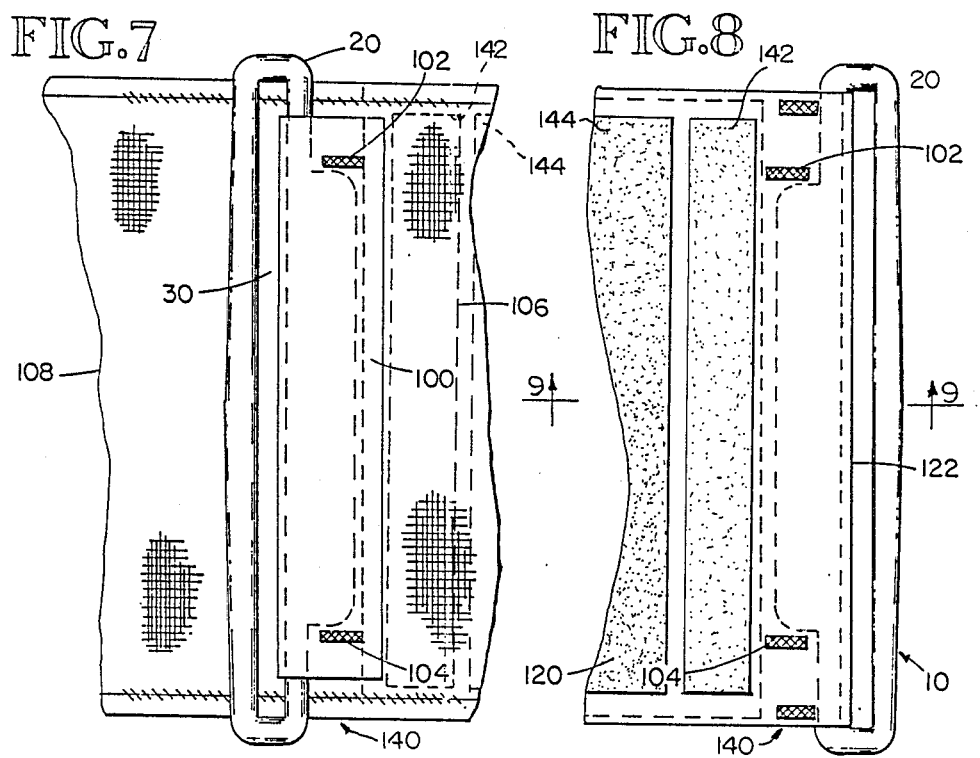

NON-BUNCHING CINCH RING FOR SELF-APPLIED BLOOD PRESSURE CUFF

TECHNICAL FIELD

The present invention relates to blood pressure cuffs used for taking blood pressure measurements and, more particularly, to self-applied cuffs that are used with the arms of human patients.

BACKGROUND ART

Blood pressure cuffs are well known in the prior art and comprise an elongated, flexible band having a predetermined length and width, a body side face and an outward face. The band is adapted to be wrapped around a limb, such as an arm or leg, to measure blood presure. Attachment means such as VELCRO TM is provided with the band to hold the band on the limb. Some self-applied cuffs include a buckle in the form of an elongated cinch ring to which one end of the band is attached and through which the other, or free, end of the band is passed to form a sleeve.

The front and back faces of the band are joined together around their peripheries to form a compartment into which an inflatable bladder is inserted. A hose portion coupled to the bladder and usually integrally formed therewith extends out from the compartment through an opening in the periphery.

When wrapping the band around the arm, it is desirable for accuracy of measurement that the center of the bladder be located over the brachial artery on the inner side of the upper arm. It has been found most convenient in ambulatory measurement applications when wrapping the band around the arm that the hose portion extend through a top periphery or edge of the cuff such that a hose coupled between the cuff and monitoring device is then routed up the front of the arm across the back of the neck to the other side of the body to the monitoring device, which is usually strapped to the patient's waist. In order to accomplish this, the slot in the periphery of the cuff is offset from the center of the bladder so that the hose portion of the bladder extends along the front of the arm.

When applying a self-applied cuff to an arm of a patient, e.g., the left arm, it has been found most convenient to insert the free end of the cuff through the buckle of the cuff at the opposite end with the fastener material on one face of the cuff facing out. This forms a sleeve into which the arm is inserted. To tighten the cuff, the user reaches under the inserted arm and pulls the free end of the cuff away from the body trunk. Then the cuff is pulled over the buckle toward the trunk and the loop and hook fastener material is pressed together. If the free end of the cuff is not pulled away at precisely the proper angle with respect to the cinch ring, the cinch ring tends to cock with respect to the length of the cuff. As a result, the cuff bunches up at one end or the other of the elongated cinch ring. This makes fitting and adjusting the cuff less convenient and more difficult for the user. It may also result in the cuff being too loose if it bunches too severely on the cinch ring.

It is desirable, therefore, to provide a cinch ring that can be used with a self-applied cuff design to overcome the tendency of the cuff to bunch up in the cinch ring.

DISCLOSURE OF THE INVENTION

The present invention relates to a self-applied blood pressure cuff adapted for use on an arm of the body. It comprises a band having a cinch ring end and a free end, a body side face and an outward face, and a compartment. The cinch ring is held in place at the cinch ring end by a loop of the cuff band that passes through the cinch ring. The length of the cinch ring exceeds the width of the cuff band so that the cinch ring freely rotates about the loop of the cinch ring end. The length of the cinch ring also exceeds the width of the free end. The compartment is open to ambient atmosphere through at least one opening on the band or through an air-permeable layer. The cuff includes an inflatable bladder adapted to be removably confined within the compartment. The bladder includes a portion which protrudes from the compartment.

In the preferred embodiment, the cuff assembly includes a cinch ring including at least one longitudinal extension and a folded-over tag piece passing through the cinch ring and extending beyond at least one of the at least one longitudinal extensions of the cinch ring. The cinch ring is transversely contained within the tag piece by reinforcing stitches sewn adjacent the longitudinally extending sides of the at least one longitudinal extension. The cuff assembly of the preferred embodiment further comprises an elongated, flexible band having first and second ends and having a body side face and an outward face. The band is formed from a web of material that is folded over and sewn longitudinally to form a longitudinal loop at the first end to define a compartment between the two faces. In addition, the cuff assembly comprises a bladder compartment within the compartment. The cuff further includes hooklike fastener material on a first area of the outward face near one end of the band with loop-like fastener material on a second area of the outward face adjacent the first area.

BRIEF DESCRIPTION OF THE DRAWINGS

FIG. 4 is a plan view of a second embodiment of the cinch ring of the present invention.

FIG. 5 is a plan view of a third embodiment of the cinch ring of the present invention.

FIG. 6 is a plan view of the cinch ring of FIG. 3 after it has been sewn into the tag piece of the present invention.

FIG. 7 is a plan view of the cinch ring and tag piece of FIG. 6 after the tag piece has been sewn into the outward face of the flexible band of the present invention.

FIG. 8 is a plan view of the first end of the blood pressure cuff assembly of the present invention after the body side face and outward face of the flexible band have been sewn together to form a bladder compartment.

BEST MODE FOR CARRYING OUT THE INVENTION

Figure 1:
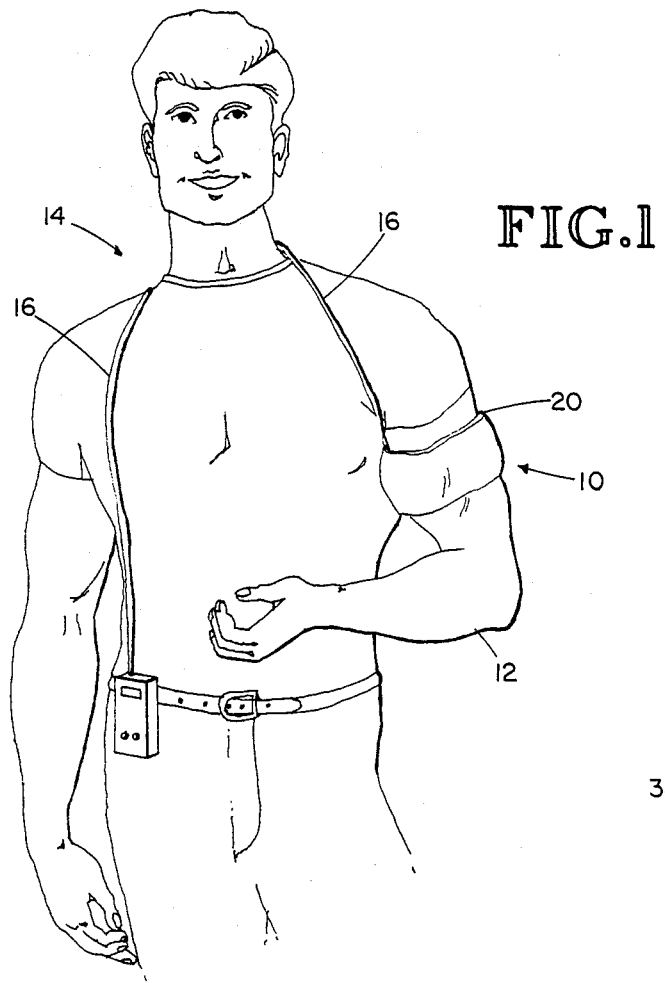
FIG. 1 is a diagram, showing a self-applied blood pressure cup assembly in use.

A diagram showing a self-applied blood pressure cuff assembly in use is shown in FIG. 1. Blood pressure cuff assembly 10 can, for example, be applied to the upper portion of the left arm 12 of a right-handed person 14.

The blood pressure cuff assembly 10 contains a bladder (not shown) that can be inflated and deflated through the application of air pressure through hose 16 that is connected to the bladder of the blood pressure cuff assembly. The bladder and hose can be made from a rubber material. In one application, the self-applied blood pressure cuff assembly 10 can be attached through hose 16 to a portable unit that periodically inflates the blood pressure cuff assembly, reads the systolic and diastolic pressures of the person 14, and records the blood pressure data for later retrieval.

The blood pressure cuff assembly 10 includes an elongated flexible band made from a flexible material. The band has two faces, a body side face and an outward face. When the cuff assembly is in use, the body side face of the flexible band is adjacent the skin of the person 14, while the outward face is directed away from the person's arm. The body side face and outward face, when sewn together, form the elongated flexible band that forms the outside of the blood pressure cuff assembly 10. The blood pressure cuff assembly can be used on a person's right arm by inverting the bladder within the blood pressure assembly 10 about an axis lying in the elongated direction of the blood pressure cuff assembly.

Figure 2:
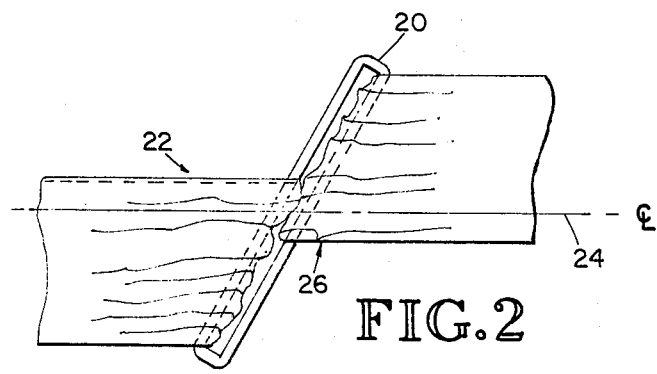
FIG. 2 is a close-up plan view showing the "bunching-up" problem of the prior art.

FIG. 2 is a close-up plan view showing the bunching up problem of self-applied blood pressure cuff assemblies of the prior art. Cinch ring 20, attached to fixed end 22 of the blood pressure cuff assembly 10 can become non-perpendicular to the longitudinal axis 24 of the blood pressure cuff assembly 10 when the cuff assembly is being applied to a person's arm. Thus, that portion of the flexible band which comprises the fixed end 22 gathers toward one end of elongated cinch ring 20. Accordingly, the portion of the free end 26 that is passing through the cinch ring 20 tends to gather toward the other end of the elongated cinch ring 20. As the material of both ends of the flexible band continues to concentrate at the respective ends of the cinch ring 20, the cinch ring 20 becomes twisted (at an angle of up to 45 degrees) with respect to the length of the person's arm. Subsequently, when the cuff assembly 10 is inflated, the bunched-up cuff material and the cinch ring 20 itself can pinch and possibly bruise the person's arm.

Figure 3:
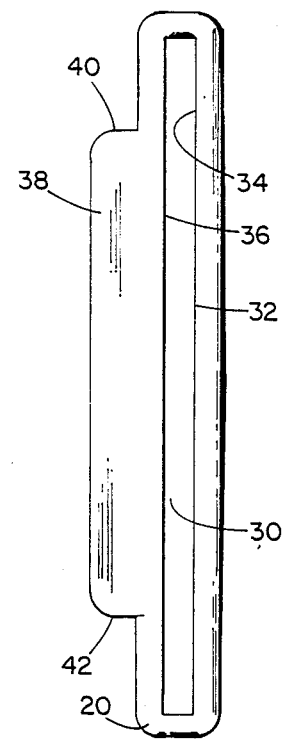
FIG. 3 is a plan view of one embodiment of the cinch ring of the prior art.

FIG. 3 is a plan view of a first embodiment of the cinch ring 20. In this embodiment, cinch ring 20 comprises an elongated ring with a slot 30. The transverse length of the slot 30 must be at least equal to the width of the free end 26 of the blood pressure cuff assembly 10. A perimeter 32 includes two long essentially parallel edges, outer edge 34 and inner edge 36. When the cinch ring 20 of FIG. 3 is assembled into a blood pressure cuff assembly 10, inner edge 36 of the cinch ring 20 is captured by the loop of material that forms the fixed end of the flexible band of the blood pressure cuff assembly 10. Adjacent to the part of cinch ring 20 in FIG. 3 that defines inner edge 36 is a longitudinal extension 38 that defines two longitudinally directed sides 40 and 42. The cinch ring 20 of FIG. 3 can be thin relative to its planar dimensions. Cinch ring 20 can, for example, be stamped from metal such as anodized aluminum or formed from a stiff plastic material.

A second embodiment of the cinch ring of the present invention is shown in the plan view of FIG. 4. The slot 50 is elongated transversely to the longitudinal direction of the blood pressure cuff assembly 10. The perimeter 52 includes outer edge 54 and inner edge 56. The edges 54 and 56 are substantially parallel. Cinch ring 20 of FIG. 4 further comprises a longitudinal extension 58 that is adjacent the portion of the cinch ring 20 that defines inner edge 56. The cinch ring 20 of FIG. 4 is substantially planar, including the longitudinal extension 58. The longitudinal extension 58 includes an aperture 60 that is defined, in part, by longitudinally directed sides 62 and 64. The outer perimeter of longitudinal extension 58 is also defined, in part, by longitudinally directed sides 66 and 68. The outer edge 54 of the cinch ring 20 of FIG. 4 can be serrated, as shown. The serrated outer edge 54 increases the friction between the cinch ring 20 and fabric of the free end 26 of blood pressure cuff assembly 10. This increased friction further counteracts the tendency of the free end 26 to slip transversely with respect to the cinch ring 20, thereby combating the undesired bunching up effect.

FIG. 5 is a plan view of a third embodiment of the cinch ring of the present invention. In this embodiment, the cinch ring 20 includes a slot 80 whose perimeter 82 is surrounded, in part, by outer edge 84 and inner edge 86. The cinch ring 20 of FIG. 5 further includes two longitudinal extensions 88 defined, in part, by longitudinally directed sides 90 and 92.

The longitudinally directed sides 40 and 42, 62–68, and 90–92 in FIGS. 3–5, respectively, is captured in order to substantially restrict transverse movement of the cinch ring with respect to the flexible band of the blood pressure cuff assembly 10. The cinch ring 20 of FIG. 3, which is substantially restricted in the longitudinal direction with respect to the flexible band of the blood pressure cuff assembly 10 can also be substantially restricted in the transverse direction by sewing reinforcing stitches between the body side face and the outward face of the flexible band of the blood pressure cuff assembly 10.

The transverse movement of the cinch ring 20 shown in FIG. 4 can be substantially restricted in two ways. One way is to set reinforcing stitches between the body side face and the outward face of the elongated flexible band adjacent longitudinally directed sides 62 and 64 as well as elsewhere within aperture 60. The other way is to sew reinforcing stitches between the body side and the outward face adjacent longitudinally directed sides 66 and 68. Of course, sewing reinforcing stitches adjacent all four longitudinally directed sides 62–68 will also restrict transverse movements of the cinch ring with respect to the flexible band.

Transverse movement of the cinch ring of FIG. 5 can be restricted with respect to the flexible band by sewing a reinforcing stitch adjacent to at least one of the longitudinally directed sides 90 and at least one of the longitudinally directed sides 92.

In the case of the cinch rings shown in FIGS. 3–5, whereas transverse movements of the cinch ring are substantially restricted by the placement of reinforcing stitches adjacent at least two longitudinally directed sides, the cinch ring may still possibly move longitudinally, depending upon the longitudinal placement of the reinforcing stitches.

FIG. 6 is a plan view of the cinch ring 20 of FIG. 3 after the cinch ring has been sewn into a tag piece. The tag piece 100 is a piece of sewable material passing through the slot of the cinch ring and covering its longitudinal extension. The use of the tag piece 100 in conjunction with the cinch ring 20 allows the cinch ring to be attached to the flexible band by being stitched to only one face of the flexible band. Thus, as shown in the plan view of FIG. 7, the cinch ring can be attached to the web of material that will form the elongated flexible band of the blood pressure cuff assembly 10 by a reinforcing stitches 102 and 104. The reinforcing stitches 102 and 104 attach the tag piece to the outward face 106 of the web of material and simultaneously substantially restrict the transverse movements of the cinch ring with respect to the flexible band. The flexible band is completed by passing the body side face 108 of the web of material through the slot 30 of the the cinch ring 20. This leaves the longitudinal edges of the outward face 106 and body side face 108 parallel to one another and forming a loop of material through the ring 20. Then the outward face 106 and the body side face 108 can be sewn together along their parallel, longitudinally directed edges to form a pocket. A first area 142 of the flexible band, which is on the outward face 106, adjacent the fixed first end 140, and covered with hook-like fastener material is adjacent a second area 144, also on the outward face 106. The second area 144 is covered with loop-like fastener material.

FIG. 8 is a close-up plan view of the fixed end of the blood pressure cuff assembly 10 of the present invention. The compartment 120 extends essentially to the loop of material 122 since the reinforcing stitches 102 and 104 do not extend between the outward cover and the body sided cover. This configuration virtually eliminates the wasted length in the prior art which resulted because the bladder compartment could not extend to the loop of material 122 as a result of the reinforcing stitches between the outward face and the body side face. Eliminating the wasted length allows the cuff to be used with a wide acceptable range of arm circumferences. The other, free, end of the flexible band (not shown) can be passed through the cinch ring 20 and folded back so that the loop-like fastener material in the second area 144 can be brought into mating engagement with the hook-like fastener material in the first area 142 (Also, see FIG. 9).

Figure 9:
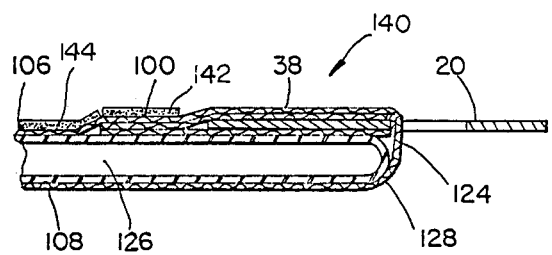
FIG. 9 is a longitudinal cross-sectional view of the fixed end of the blood pressure cuff assembly of FIG. 8.

A further advantage of tag piece 100 is shown in the longitudinal cross-sectional view of the fixed end of the blood pressure cuff assembly 10 given in FIG. 9. The tag piece 100 is attached to the outward cover 106 by reinforcing stitches 102 and 104. Therefore, the end 124 of bladder 126 can be placed adjacent the loop of material 128 that passes through cinch ring 20 and between body side cover 108 and the longitudinal extension 38. Therefore, when the blood pressure cuff assembly 10 is inflated, the bladder 126 will force the longitudinal extension 38 outwardly from the body side cover 108. This reduces the discomfort of the person whose blood pressure is being taken due to forcing longitudinal extension 38 against the person's body.

While those skilled in the art will readily appreciate that many modifications of the embodiments of the present invention described above can be made, the spirit and scope of the present invention is to be limited only by the following claims.

I claim:

1. A self-applied blood pressure cuff assembly, comprising:
    an elongated, flexible band having first and second ends, two longitudinal edges extending between the first and second ends, and a body side face and an outward face, the faces extending between the two longitudinal edges, the band having a compartment between the body side face and the outward face, the first end comprising a longitudinal loop;
    a bladder contained within the compartment; and
    a cinch ring captured by the longitudinal loop, the cinch ring including at least one longitudinal extension contained within the flexible band and extending toward the second end of the flexible band, the at least one longitudinal extension being captured to substantially restrict transverse movements of the cinch ring with respect to the flexible band and having two longitudinally-directed sides that are transversely separated.

2. The self-applied blood pressure cuff assembly of claim 1 wherein the second end of the elongated flexible band is captured through the cinch ring.

3. The self-applied blood pressure cuff assembly of claim 1 wherein the cinch ring has one longitudinal extension, the two longitudinally directed sides of the longitudinal extension being transversely separated by a distance that is slightly less than the width of the flexible band at the first end.

4. The self-applied blood pressure cuff assembly of claim 3 wherein the two longitudinally directed sides of the longitudinal extension are captured by a reinforcing stitch sewn through the two faces of the flexible band.

5. The self-applied blood pressure cuff assembly of claim 1 wherein a longitudinal extension of the cinch ring comprises an aperture having two inner longitudinally directed sides.

6. The self-applied blood pressure cuff assembly of claim 5 wherein the two inner longitudinally directed sides of the aperture are captured by reinforcing stitches sewn through the two faces of the flexible band.

7. A self-applied blood pressure assembly, comprising:
    an elongated, flexible band having first and second ends, two longitudinal edges extending between the first and second ends, and a body side face and an outward face, the faces extending between the two longitudinal edges, the band being formed from a web of material which is folded over and sewn longitudinally to form a longitudinal loop at the first end to define a compartment between the two faces;
    a bladder contained within the compartment; and
    a cinch ring having an inner perimeter that is captured by the longitudinal loop, the cinch ring including at least one longitudinal extension contained within the flexible band and extending toward the second end of the flexible band, the at least one longitudinal extension being captured to substantially restrict transverse movements of the cinch ring with respect to the flexible band and having two longitudinally directed sides that are transversely separated.

8. The self-adjusting blood pressure cuff assembly of claim 7 wherein the two longitudinally directed sides of the longitudinal extension are captured by a reinforcing stitch sewn through the two faces of the flexible band.

9. The self-applied blood pressure cuff assembly of claim 7 wherein a longitudinal extension of the cinch ring comprises an aperture having two inner longitudinally directed sides.

10. The self-applied blood pressure cuff assembly of claim 9 wherein the two inner longitudinally-directed sides of the aperture are captured by reinforcing stitches sewn through the faces of the flexible band.

11. The self-applied blood pressure cuff assembly of claim 7 wherein the inner perimeter of the cinch ring is at least partially serrated.

12. The self-applied blood pressure cuff assembly of claim 7 wherein the bladder is adjacent the loop of the web of material.

13. A self-applied blood pressure assembly, comprising:
   a cinch ring having an inner perimeter and including at least one longitudinal extension, the at least one longitudinal extension having two longitudinally directed sides that are transversely separated;
   a folded-over tag piece passing through the cinch ring and extending beyond the at least one longitudinal extension of the cinch ring, the cinch ring being transversely contained within the tag piece by reinforcing stitches sewn adjacent the longitudinally directed sides of the at least one longitudinal extension;
   an elongated, flexible band having first and second ends and have a body side face and an outward face, the band being formed from a web of material which is folded over and sewn longitudinally to form a longitudinal loop at the first end to define a compartment between the two faces, the flexible band passing through the cinch ring and enclosing the cinch ring in its first end, the tag piece and the outward face of the flexible band being sewn together; and
   a bladder contained within the compartment.

14. The self-applied blood pressure cuff assembly of claim 13 wherein the second end of the elongated, flexible band is captured through the cinch ring.

15. The self-applied blood pressure cuff assembly of claim 13 wherein the longitudinally directed sides of the longitudinal extension are captured by a reinforcing stitch sewn through the two faces of the flexible band.

16. The self-applied blood pressure cuff assembly of claim 13 wherein a longitudinal extension of the cinch ring comprises an aperture having two inner longitudinally directed sides.

17. The self-applied blood pressure cuff assembly of claim 16 wherein the two inner longitudinally-directed sides of the aperture are captured by reinforcing stitches sewn through the two faces of the flexible band.

18. The self-applied blood pressure cuff assembly of claim 13 wherein the inner perimeter of the cinch ring is serrated.

19. The self-applied blood pressure cuff assembly of claim 13 wherein the bladder is adjacent the loop of the web of material.

20. A self-applied blood pressure cuff assembly, comprising:
   a cinch ring having an inner perimeter and including at least one longitudinal extension, the inner perimeter of the cinch ring being serrated and the at least one longitudinal extension having two longitudinally directed sides that are transversely separated;
   a folded-over tag piece passing through the cinch ring and extending beyond the at least one longitudinal extension of the cinch ring, the cinch ring being transversely contained within the tag piece by reinforcing stitches sewn adjacent the longitudinally directed sides of the at least one longitudinal extension;
   an elongated, flexible band having first and second ends and having a body side face and an outward face, the band being formed from a web of material which is folded over and sewn longitudinally to form a longitudinal loop at the first end and to define a compartment between the two faces, the flexible band passing through the cinch ring and enclosing the cinch ring in its first end, the tag piece and the outward face of the flexible band being sewn together; and
   a bladder contained within the compartment, the bladder being adjacent the loop of the web of material.

21. The self-applied blood pressure cuff assembly of claim 20 wherein the cuff further comprises hook-like fastener material on a first area of the outward face adjacent the first end and loop-like fastener material on a second area of the outward face adjacent the first area for mating engagement with the hook-like fastener material.

* * * * *